(12) United States Patent
Phan et al.

(10) Patent No.: US 8,157,842 B2
(45) Date of Patent: Apr. 17, 2012

(54) INTERSPINOUS IMPLANT AND METHODS OF USE

(75) Inventors: Christopher U. Phan, San Leandro, CA (US); Avram A. Edidin, Portola Valley, CA (US); Lauren I. Lyons, Sunnyvale, CA (US); Tanmay Mishra, Mountain View, CA (US)

(73) Assignee: Kyphon SARL, Neuchatel (CH)

( * ) Notice: Subject to any disclaimer, the term of this patent is extended or adjusted under 35 U.S.C. 154(b) by 274 days.

(21) Appl. No.: 12/483,812

(22) Filed: Jun. 12, 2009

(65) Prior Publication Data
US 2010/0318127 A1    Dec. 16, 2010

(51) Int. Cl.
*A61B 17/70* (2006.01)
(52) U.S. Cl. ........................................................ 606/249
(58) Field of Classification Search ............... 606/249, 606/279; 623/17.11, 17.15
See application file for complete search history.

(56) References Cited

U.S. PATENT DOCUMENTS

| | | |
|---|---|---|
| 624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |
| 3,065,659 A | 11/1962 | Eriksson et al. |
| 3,108,595 A | 10/1963 | Overment |
| 3,242,922 A | 3/1966 | Thomas |
| 3,426,364 A | 2/1969 | Lumb |
| 3,648,691 A | 3/1972 | Lumb et al. |
| 3,779,239 A | 12/1973 | Fischer et al. |
| 4,011,602 A | 3/1977 | Rybicki et al. |
| 4,237,875 A | 12/1980 | Termanini |

(Continued)

FOREIGN PATENT DOCUMENTS
DE    2821678 A1    11/1979
(Continued)

OTHER PUBLICATIONS

Kramer et al., "Intervetertebral Disk Diseases: Causes, Diagnosis, Treatment and Prophylaxis," pp. 244-249, Medical, 1990.

(Continued)

*Primary Examiner* — Eduardo C Robert
*Assistant Examiner* — Stuart S Bray

(57) ABSTRACT

Vertebral implants sized to be inserted into a patient and positioned in an interspinous space. The implants may include a body and a pair of wings that extend outward beyond a first side of the body. The implants are sized and configured for the body to be positioned in the interspinous space with the wings on opposing lateral sides of one of the spinous processes. The wings may be adjusted to various spaced-apart distances to be positioned on the opposing sides of the spinous process. The implants may further be selectively adjustable between a collapsed orientation and a deployed orientation. The collapsed orientation includes one or both wings aligned with the main body to reduce an overall size of the implant to facilitate insertion into a patient. The extended orientation includes the wings extending outward from the first side of the body and along the lateral sides of the spinous process.

9 Claims, 8 Drawing Sheets

U.S. PATENT DOCUMENTS

| | | |
|---|---|---|
| 4,257,409 A | 3/1981 | Bacal et al. |
| 4,274,324 A | 6/1981 | Giannuzzi |
| 4,289,123 A | 9/1981 | Dunn |
| 4,401,112 A | 8/1983 | Rezaian |
| 4,519,100 A | 5/1985 | Wills et al. |
| 4,553,273 A | 11/1985 | Wu |
| 4,554,914 A | 11/1985 | Kapp et al. |
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 5,000,165 A | 3/1991 | Watanabe |
| 5,000,166 A | 3/1991 | Karpf |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,127,912 A | 7/1992 | Ray et al. |
| 5,171,278 A | 12/1992 | Pisharodi |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,360,430 A | 11/1994 | Lin |
| 5,366,455 A | 11/1994 | Dove |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,458,641 A | 10/1995 | Ramirez Jimenez |
| 5,470,333 A | 11/1995 | Ray |
| 5,480,442 A | 1/1996 | Bertagnoli |
| 5,496,318 A | 3/1996 | Howland et al. |
| 5,518,498 A | 5/1996 | Lindenberg et al. |
| 5,554,191 A | 9/1996 | Lahille et al. |
| 5,562,662 A | 10/1996 | Brumfield et al. |
| 5,562,735 A | 10/1996 | Margulies |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,800,547 A | 9/1998 | Schafer et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,068,630 A | 5/2000 | Zucherman et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,190,413 B1 | 2/2001 | Sutcliffe |
| 6,190,414 B1 | 2/2001 | Young |
| 6,197,028 B1 | 3/2001 | Ray et al. |
| 6,214,050 B1 | 4/2001 | Huene |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,704 B1 | 7/2002 | Ferree |
| 6,440,169 B1 | 8/2002 | Elberg et al. |
| 6,447,513 B1 | 9/2002 | Griggs |
| 6,451,019 B1 | 9/2002 | Zucherman et al. |
| 6,500,178 B2 | 12/2002 | Zucherman et al. |
| 6,514,256 B2 | 2/2003 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,685,742 B1 | 2/2004 | Jackson |
| 6,695,842 B2 | 2/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,534 B2 | 5/2004 | Sherman |
| 6,736,818 B2 | 5/2004 | Perren et al. |
| 6,740,088 B1 | 5/2004 | Kozak et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,793,658 B2 | 9/2004 | LeHuec et al. |
| 6,835,205 B2 | 12/2004 | Atkinson et al. |
| 6,884,242 B2 | 4/2005 | LeHuec et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,081,120 B2 | 7/2006 | Li et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |

| | | |
|---|---|---|
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 2001/0016743 A1 | 8/2001 | Zucherman et al. |
| 2002/0143331 A1 | 10/2002 | Zucherman et al. |
| 2002/0147450 A1 | 10/2002 | LeHuec et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2004/0010312 A1 | 1/2004 | Enayati |
| 2004/0087947 A1 | 5/2004 | Lim et al. |
| 2004/0097931 A1 | 5/2004 | Mitchell |
| 2004/0133204 A1 | 7/2004 | Davies |
| 2004/0133280 A1 | 7/2004 | Trieu |
| 2004/0153071 A1 | 8/2004 | Zucherman et al. |
| 2004/0167625 A1 | 8/2004 | Beyar et al. |
| 2004/0172029 A1* | 9/2004 | Lerch ............................ 606/71 |
| 2004/0199255 A1 | 10/2004 | Mathieu et al. |
| 2004/0210221 A1 | 10/2004 | Kozak et al. |
| 2004/0260397 A1 | 12/2004 | Lambrecht et al. |
| 2005/0010293 A1 | 1/2005 | Zucherman et al. |
| 2005/0049708 A1 | 3/2005 | Atkinson et al. |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1* | 10/2006 | Butler et al. ................ 623/17.15 |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0271061 A1 | 11/2006 | Beyar et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0032790 A1* | 2/2007 | Aschmann et al. ............ 606/61 |
| 2007/0043362 A1 | 2/2007 | Malandain et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0161993 A1 | 7/2007 | Lowery et al. |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0203491 A1 | 8/2007 | Pasquet et al. |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233088 A1 | 10/2007 | Edmond |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0021457 A1 | 1/2008 | Anderson et al. |
| 2008/0021460 A1 | 1/2008 | Bruneau et al. |
| 2008/0058934 A1 | 3/2008 | Malandain et al. |
| 2008/0108990 A1* | 5/2008 | Mitchell et al. ................ 606/61 |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0132952 A1 | 6/2008 | Malandain et al. |
| 2008/0140125 A1 | 6/2008 | Mitchell et al. |
| 2008/0147190 A1 | 6/2008 | Dewey et al. |
| 2008/0147192 A1 | 6/2008 | Edidin et al. |
| 2008/0161818 A1 | 7/2008 | Kloss et al. |
| 2008/0167685 A1 | 7/2008 | Allard et al. |
| 2008/0177312 A1 | 7/2008 | Perez-Cruet et al. |
| 2008/0183211 A1 | 7/2008 | Lamborne et al. |
| 2008/0183218 A1 | 7/2008 | Mueller et al. |
| 2008/0215094 A1 | 9/2008 | Taylor |
| 2008/0221685 A9 | 9/2008 | Altarac et al. |
| 2008/0221692 A1 | 9/2008 | Zucherman et al. |
| 2008/0262617 A1 | 10/2008 | Froehlich et al. |
| 2008/0281360 A1 | 11/2008 | Vittur et al. |
| 2008/0281361 A1 | 11/2008 | Vittur et al. |
| 2008/0319550 A1 | 12/2008 | Altarac et al. |
| 2009/0062915 A1 | 3/2009 | Kohm et al. |
| 2009/0105773 A1 | 4/2009 | Lange et al. |
| 2009/0234389 A1* | 9/2009 | Chuang et al. ................ 606/249 |
| 2009/0270918 A1 | 10/2009 | Attia et al. |
| 2009/0292316 A1* | 11/2009 | Hess ............................ 606/249 |
| 2010/0121379 A1 | 5/2010 | Edmond |

FOREIGN PATENT DOCUMENTS

| | | |
|---|---|---|
| DE | 3922044 A1 | 2/1991 |
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084768 A2 | 10/2004 |
| WO | WO 2004/110300 A2 | 12/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007052975 A1 | 5/2007 |
| WO | WO 2008/029260 | 3/2008 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

Zdeblick et al., "Two-Point Fixation of the Lumbar Spine Differential Stability in Rotation," SPINE, 1991, pp. S298-S301, vol. 16, No. 6, Supplement.

"Dispositivo Intervertebrale Ammortizzante DIAM," date unknown, p. 1.

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerative del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrates Lombaires, Gastambide, ed., 1995, pp. 122-132, Expansion Scientifique Française, Paris, France.

Senegas, "La Ligamentoplastie Inter Vertébrate Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodése dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une experience clinique d'un implant postérieur amortissant," Rachis Revue de Pathologie Vertébrate, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

\* cited by examiner

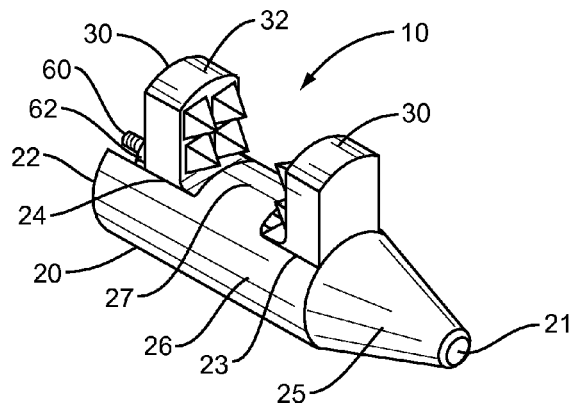
FIG. 1
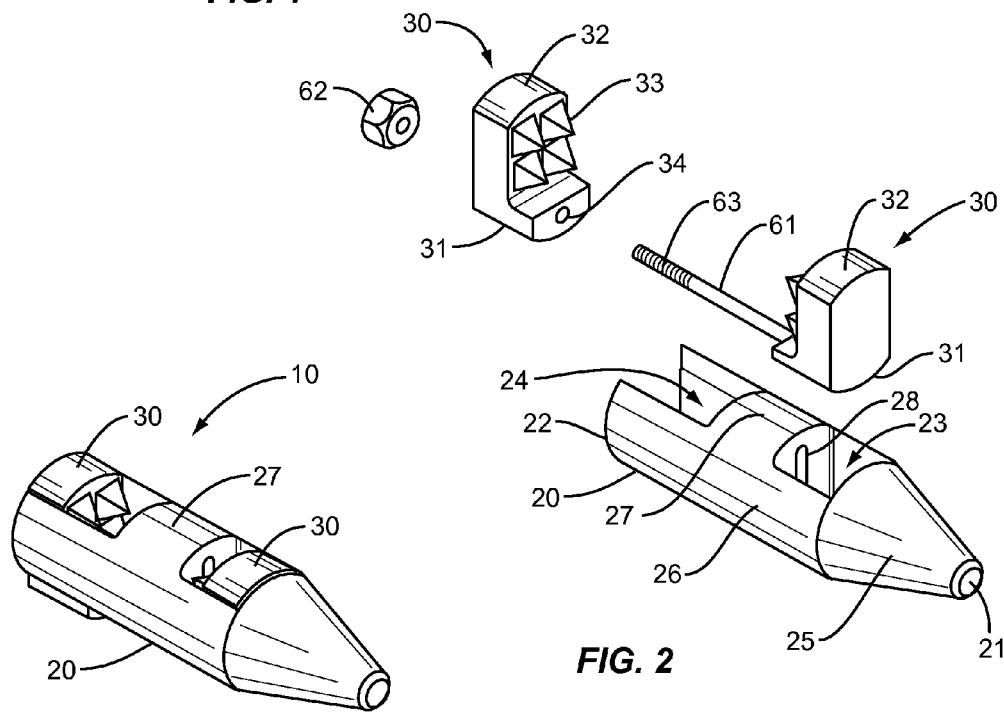
FIG. 2
FIG. 3
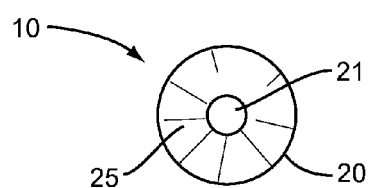
FIG. 4A
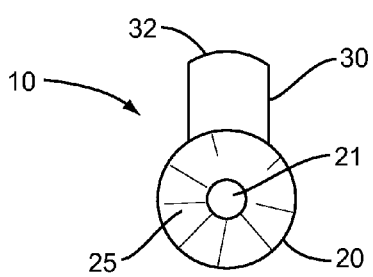
FIG. 4B

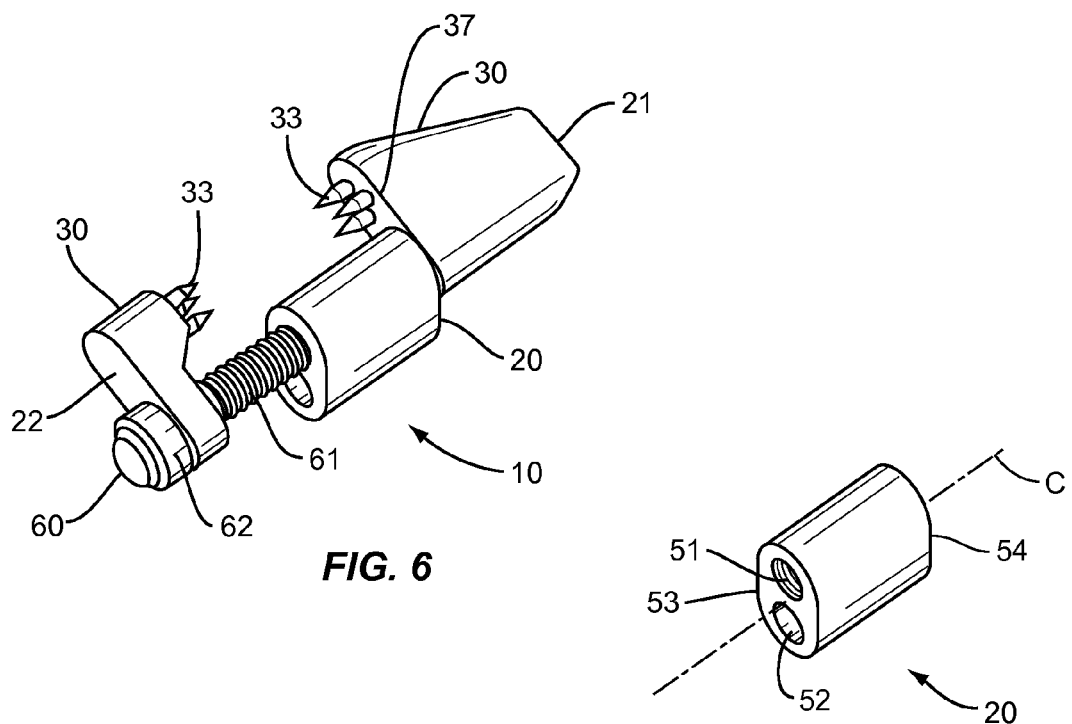
FIG. 6
FIG. 7
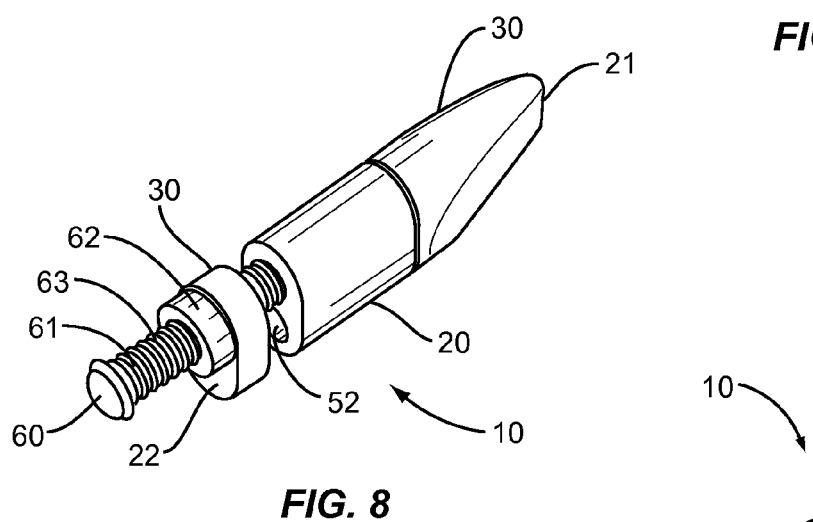
FIG. 8
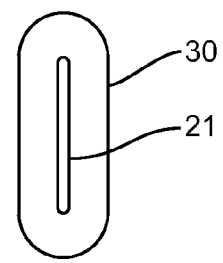
FIG. 9

INTERSPINOUS IMPLANT AND METHODS OF USE

BACKGROUND

The invention relates generally to the treatment of spinal conditions, and more particularly, to the treatment of spinal conditions using an implant configured for insertion into an interspinous space. The implant is adjustable between a closed orientation with a reduced size to facilitate insertion into the patient and a deployed orientation with an enlarged size to maintain the position within the patient.

A significant portion of the population will experience back pain at some point in their lives resulting from a spinal condition. The pain may range from general discomfort to disabling pain that immobilizes the individual. Back pain may result from a trauma to the spine, be caused by the natural aging process, or may be the result of a degenerative disease or condition.

Procedures to remedy back problems sometimes require correcting the distance between vertebral members by inserting an interspinous device (e.g., spacer) between spinous processes. In some instances, implants are positioned between the spinous processes of the L5 and S1 vertebral members. However, current implants often cannot be used in this space because of the huge variations in the sacral anatomy and the lack of an S1 spinous process in about 70% of the population.

Further, insertion of an interspinous implant often requires extensive surgical techniques. These implants often require an open technique to be implanted, and many require destroying important anatomical stabilizers, such as the supraspinous ligament. In particular, some techniques for placing such implants is to cut the interspinous and supraspinous ligaments and slide the device over the adjacent spinous processes.

Therefore, there is a need for an implant that can be positioned in the interspinous space, and also can be implanted in a less intrusive manner.

SUMMARY

The present application is directed to implants for insertion into an interspinous space. The implants may be used in the interspinous space formed between the L5 spinous process and a sacrum, and in interspinous spaces formed between spinous processes at various other spinal levels. The implant includes a body with a first side that faces towards the first spinous process and a second side that faces towards the second spinous process. The body may include a compliant material that contacts against one or both of the spinous processes when the body is positioned in the interspinous space. The implant further includes a first wing positioned in proximity to the leading end and away from the trailing end. The first wing may be movably connected to the body and selectively positionable from a closed orientation positioned at the first side of the body to a deployed orientation extending outward above the first side of the body. The implant may further include a second wing positioned in proximity to the trailing end and away from the leading end. The second wing may extend outward above the first side of the body when the first wing is in the deployed orientation. The implant may also include a deploying mechanism operatively connected to at least the first wing, and may also be connected to the second wing. The deploying mechanism may move one or both of the wings from the closed orientation to the deployed orientation. The deploying mechanism may also move one or both wings to reduce a distance between the wings and into contact with the spinous process. Each of the first and second wings may be positioned above a second side of the body when the first wing is in the deployed orientation.

The various aspects of the various embodiments may be used alone or in any combination, as is desired.

BRIEF DESCRIPTION OF THE DRAWINGS

FIG. 1 is a perspective view of an implant in a deployed orientation according to one embodiment.

FIG. 2 is an exploded perspective view of an implant according to one embodiment.

FIG. 3 is a perspective view of an implant in a closed orientation according to one embodiment.

FIG. 4A is a front view of an implant in a closed orientation according to one embodiment.

FIG. 4B is a front view of an implant in a deployed orientation according to one embodiment.

FIG. 6 is a perspective view of an implant in a deployed orientation according to one embodiment.

FIG. 7 is a perspective view of a body of an implant according to one embodiment.

FIG. 8 is a perspective view of an implant in a closed orientation according to one embodiment.

FIG. 9 is a front view of an implant in a closed orientation according to one embodiment.

DETAILED DESCRIPTION

Figure 5A:
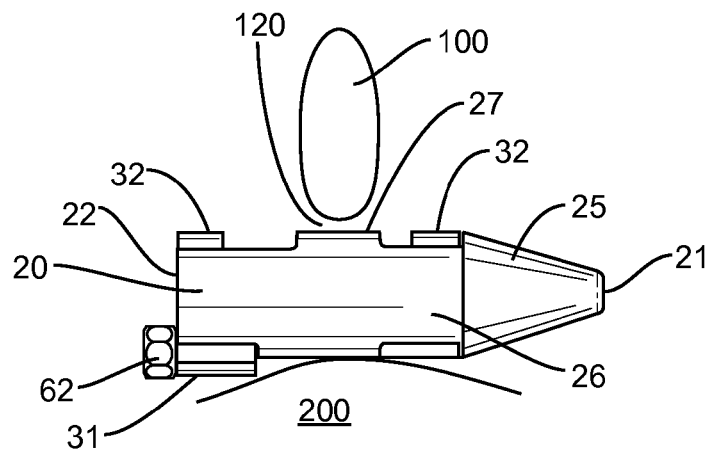
FIG. 5A is a side view of an implant in a closed orientation inserted within a patient according to one embodiment.

The present application is directed to implants for insertion into the interspinous space formed between first and second vertebral members. The implants include a main body and a pair of wings that extend outward from the body. The implants are sized and configured for the main body to be positioned along a centerline of the spine with the wings on opposing lateral sides of a spinous process of the first vertebral member. The body may contact or may be spaced from the second vertebral member. The implants may further be selectively adjustable between a collapsed orientation and an extended orientation. The collapsed orientation features one or both wings aligned in proximity with the main body to reduce an overall size of the implant to facilitate insertion into the patient. The extended orientation includes the wings extending outward from the body for positioning against the first spinous process.

The implants may include various configurations of bodies and wings. FIGS. 1-3 illustrate an implant 10 with a body 20, first and second wings 30, and a deployment mechanism 60. The body 20 includes an elongated shape with a first end 21 and a second end 22. The body 20 also includes a first section 25 at the first end 21 that may include a tapered shape that facilitates insertion of the implant 10 into the patient. The first section 25 may include various cross-sectional shapes. In one embodiment, the first section 25 is not tapered. The first end 21 may be substantially flat, or may include a point. The body 20 also includes a second section 26. In the embodiment of FIGS. 1-3, the second section 26 is cylindrical, although it may also include various other cross-sectional shapes, including but not limited to elliptical and oblong The first section 25 may be sized to increase in cross-sectional size and provide a smooth transition to the second section 26.

Recesses 23, 24 are positioned in the body 20 to receive the wings 30. The recesses 23, 24 are spaced apart by a gap 27 sized to accommodate the first spinous process. The illustrated embodiment includes each of the recesses 23, 24 positioned along the second section 26. The first recess 23 is positioned at a first end of the second section 26 and is positioned at the transition with the first section 25, and the second recess 24 extends into the second section 26 from the second end 22. The recesses 23, 24 may extend completely through the body 20, or may extend a limited depth inward from the superior surface.

As illustrated in FIG. 2, a slot 28 extends through the body 20 between the recesses 23, 24. The slot 28 is positioned within an interior of the body 20 under the exterior surface of the gap 27.

The wings 30 are sized to fit within the recesses 23, 24. The wings 30 include a first end 31 and a second end 32. One or both ends 31, 32 may include a rounded shape that corresponds to the rounded exterior surface of the body 20. The wings 30 may be substantially identical, or may include different shapes, sizes, and features. Wings 30 may also include teeth 33 that extend laterally outward from an inner side. The teeth 33 are configured to engage with the spinous process of the first vertebral member and may include various shapes and sizes. The embodiments of FIGS. 1-3 include teeth 33 on each of the wings 30, although teeth 33 may be included on just one of the wings 30. The teeth 33 may include various shapes other than those illustrated, including but not limited to ridges and knurled sections. In one embodiment, the teeth 33 on the first wing 30 are offset from the teeth 33 on the second wing 30. The offset positioning prevents the teeth from contacting together when the wings 30 are engaged with the spinous process.

The deployment mechanism 60 moves the wings 30 between the closed orientation as illustrated in FIG. 3 and the deployed orientation as illustrated in FIG. 1. The deployment mechanism 60 may also laterally move the wings 30 relative to each other for attachment to the spinous process of the superior vertebral member.

FIG. 2 illustrates a deployment mechanism 60 that includes a rod 61 and a fastener 62. The rod 61 includes an elongated shape with a threaded section 63. The rod 61 is attached to the first wing 30 and includes a length to extend through the slot 28 and at least into the opposing recess 24. The rod 61 is sized to fit through an aperture 34 in the second wing 30 with the threaded section 63 at least partially extending outward from the second wing 30. The fastener 62 is threaded onto the threaded section 63. Fastener 62 may be a nut that attaches to the rod 61. The rod 61 may include one or more weakened sections, including a reduced cross-sectional size. The weakened sections are positioned along the section that extends outward beyond the fastener 62. The surgeon can apply a force to the appropriate section to reduce the length of the rod 61. In one embodiment, the weakened sections are positioned such that the rod 61 does not extend outward beyond the body 20.

In the closed orientation, at least the leading wing 30 adjacent to the first section 25 is positioned within the profile formed by the body 20. FIG. 4A includes a front view of the implant 10 in the closed orientation with both wings 30 closed into the body 20. In this embodiment, the first section 25 includes a tapered shape with a maximum diameter greater than or equal to the diameter of the second section 26. Therefore, the second section 26 is not visible in this front view. This reduced size in the closed orientation facilitates insertion into the patient and adjacent to the spinous process. FIG. 4B illustrates the implant 10 in the deployed orientation with the wings 30 extending outward beyond the envelope of the body 20.

Figure 5B:
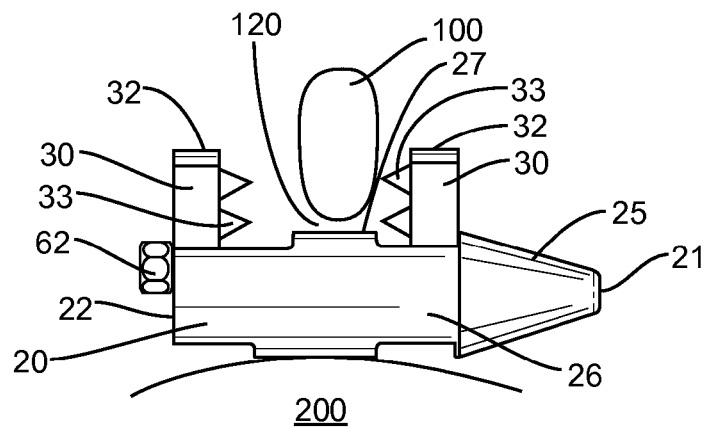
FIG. 5B is a side view of an implant in a partially deployed orientation inserted within a patient according to one embodiment.
Figure 5C:
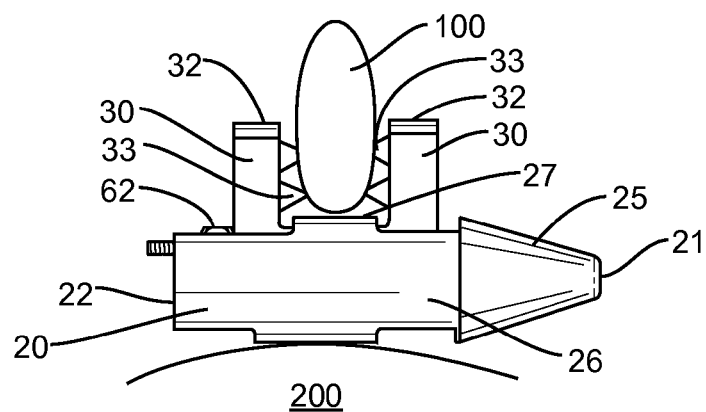
FIG. 5C is a side view of an implant in a deployed orientation inserted within a patient according to one embodiment.

FIGS. 5A-5C illustrate positioning and deployment of the implant 10 within the interspinous space 120 formed between the vertebral members 100, 200. In this embodiment, the first vertebral member 100 is an L5 vertebral member, and the second vertebral member 200 is a sacrum that does not include a spinous process adequate to support and/or position the implant 10. The implant 10 is positioned on the sacral roof of the sacrum.

The implant 10 includes a reduced size in the closed orientation as illustrated in FIG. 5A that facilitates insertion into the patient. The implant 10 may be inserted percutaneously with the use of the proper tools. The implant 10 may also be inserted through a mini-open incision that requires unilateral tissue retraction as the wings 30 are both deployed from the ipsilateral side as will be explained below. This sequence includes the fastener 62 attached to the rod 61 to connect the wings 30 together prior to insertion into the patient. In other embodiments, the rod 61 is attached to the wings 30 after insertion of the body 20 and wings 30 into the patient.

FIG. 5A includes the implant 10 positioned within the patient with the body 20 resting against the roof (i.e., superior edge) of the second vertebral member 200 which in this embodiment is the sacrum. In other embodiments, the body 20 does not contact the second vertebral member 200. The body 20 may include a height measured between superior and inferior surfaces of the second section 26 for the gap 27 on the first surface to contact the inferior edge of the spinous process of the first vertebral member 100 while the inferior surface contacts against the second vertebral member 200. The reduced size of the implant 10 in the closed orientation with the wings 30 positioned within the profile of the body 20 facilitates insertion into the patient. The conical first section 25 is shaped to ease the insertion into the space 120.

The wings 30 are enclosed within the body 20 to allow for smooth dilation and insertion through the interspinous space 120. In some instances, the wings 30 may not completely fit within the recesses 23, 24 resulting in the second ends 32 extending beyond the superior surface of the second section 26. FIG. 5A includes the first section 25 including a larger size than the second section 26 (i.e., a larger profile). Thus, even though the second ends 32 extend outward beyond the second section 26, the wings 30 are still positioned within the profile of the first section 25.

FIG. 5B includes the implant 10 in a partially deployed orientation. Deployment occurs with the surgeon applying a force in a superior direction on the fastener 62 which is exposed at the second end 22 of the body 20 through the insertion path. This force causes the fastener 62, rod 61 and attached wings 30 to move upward relative to the body 20 and the rod 61 to move along the slot 28 in the body 20.

The length of the rod 61 causes the wings 30 to be spaced apart a distance to extend outward from the body 20 along each lateral side of the spinous process 100. This spacing allows for the deploying movement without the wings 30 contacting against the spinous process 100. The extent of deployment of the wings 30 from the body 20 may vary depending upon the context of use. Full deployment occurs when the rod 61 contacts against an upper edge of the slot 28 thereby preventing further deployment movement.

In one embodiment, the body 20 and one or both wings 30 include a ratchet structure. This may include a stepped or wedged shape on each of the body 20 and wings 30. During deployment, the wings 30 move outward from the body 20 and along the ratchet structure. The wings 30 deploy in a stepped process and may be positioned at the various steps to extend outward from the body 30 the desired amount.

Once at the proper position, the fastener 62 is further threaded onto the threaded section 63 of the rod 61. The threading causes the fastener 62 to move along the length of the rod 61 and force the wings 30 together. This may include movement of both wings 30 relative to the body 20, or movement of just one wing 30 with the other wing remaining stationary relative to the body 20. In one embodiment, just the proximal wing 30 moves with the distal wing 30 remaining stationary. This movement results in the teeth 33 contacting with the spinous process 100 to attach the implant 10. The extent of inward movement of the wings 30 may vary depending upon the context. As illustrated in FIG. 5C, the fastener 62 may move along the rod 61 and beyond the second end 22 of the body 20 and into the recess 24. This portion of the rod 61 may be removed by the surgeon once the implant 10 is properly positioned in the patient.

The implant 10 may also include one or more pins to maintain the position of the wings 30. Apertures in the wings 30 and body 20 are sized to receive the pins to secure the relative positions. In one embodiment, a wedge is inserted into the slot 28 after the wings 30 are deployed. The wedge prevents the rod 61 from moving within the slot 28 and possibly causing the wings 20 to retract.

In the embodiment described above, both wings 30 are retracted in to the body 30 with the implant 10 in the closed orientation. Alternatively, just the first or leading wing 30 adjacent to the first section 25 retracts into the body 20. The second or trailing wing 30 adjacent to the second end 22 may not retract into the body 20 because this second wing 30 does not pass through the interspinous space 120 during the implantation process.

FIGS. 6-9 include an implant 10 with the body 20 movable relative to the wings 30. The body 20 includes an oval cross-sectional shape with first and second apertures 51, 52 that are each offset from a longitudinal axis C. Body 20 may also include other cross-sectional shapes, including but not limited to circular, elliptical, and rectangular.

The first or leading wing 30 includes a tapered shape that extends between a reduced first end 21 and an enlarged second end 37. The second end 37 includes a cross-sectional shape that is larger than or equal to the body 20. Further, teeth 33 extend outward from a small area of the second end 37 and face towards the second or trailing wing 30. The second wing 30 includes an elongated cross-sectional shape that may be the same as the second end 37. Teeth 33 also extend outward from a small area and face towards the first wing 30. The teeth 33 are aligned on the wings 30 to fit within the aperture 52 of the body 20 when the implant 10 is in the closed orientation.

The deploying mechanism 60 includes a rod 61 that is connected to the first wing 30 and extends through the body 20 and second wing 30. A fastener 62 is threaded onto a threaded section 63 at the end of the rod 61.

The implant 10 is inserted into the patient in the closed orientation as illustrated in FIG. 8. The body 20 is aligned with the wings 30 and positioned within the profile of at least the first wing 30. This orientation places the teeth 33 on the wings 30 within the aperture 52, with the rod 61 extending through the aperture 51 of the body 20 and the second wing 30. FIG. 9 illustrates a front view of the implant 10 in the closed orientation with the body 20 and second wing 30 within the profile of the first wing 30. The implant 10 is inserted with the first wing 30 moving through the space 120 and aligning along a first lateral side of the spinous process of the first vertebral member 100, the second wing 30 on a second lateral side of the spinous process, and the body 20 aligning within the space 120.

Once positioned, the wings 30 are rotated relative to the body 30 with the first wing 30 rotating along a first lateral side of the spinous process 100 and the second wing 30 rotating along a second lateral side. This rotation causes the body 20 to move out of the profile of the wings 30. The rotation may be caused by the surgeon manipulating the rod 61 and applying the rotational force. Once the wings 30 are in position, the fastener 62 is threaded along the rod 61 and moving the wings 30 towards each other. The teeth 33 may move into contact with the spinous process of the first vertebral member 100 to maintain the position of the implant 10.

Figure 21:
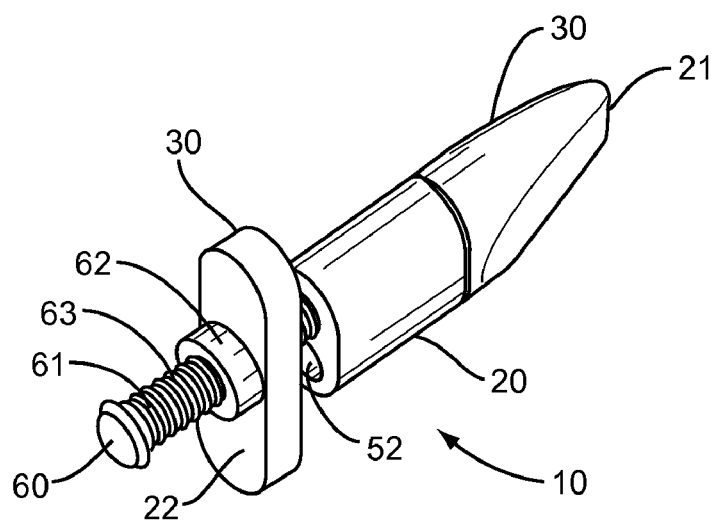
FIG. 21 is a perspective view of an implant in a closed orientation according to one embodiment.

FIG. 21 includes an embodiment with the trailing wing 30 including a greater length than the body 20. This length may extend outward from a single side of the body 20 when the implant 10 is in the closed orientation, or may extend outward on opposing sides of the body 20. FIG. 21 includes the wing 30 extending outward from both sides. The trailing wing 30 is not moved into or through the interspinous space 120 and therefore may be longer than the body 20 and/or first wing 30. The increased length of the trailing wing 30 facilitates placement of the implant 10 within the interspinous space 120. In this embodiment, the one or both of the wings 30 may not include teeth 33.

Figure 10:
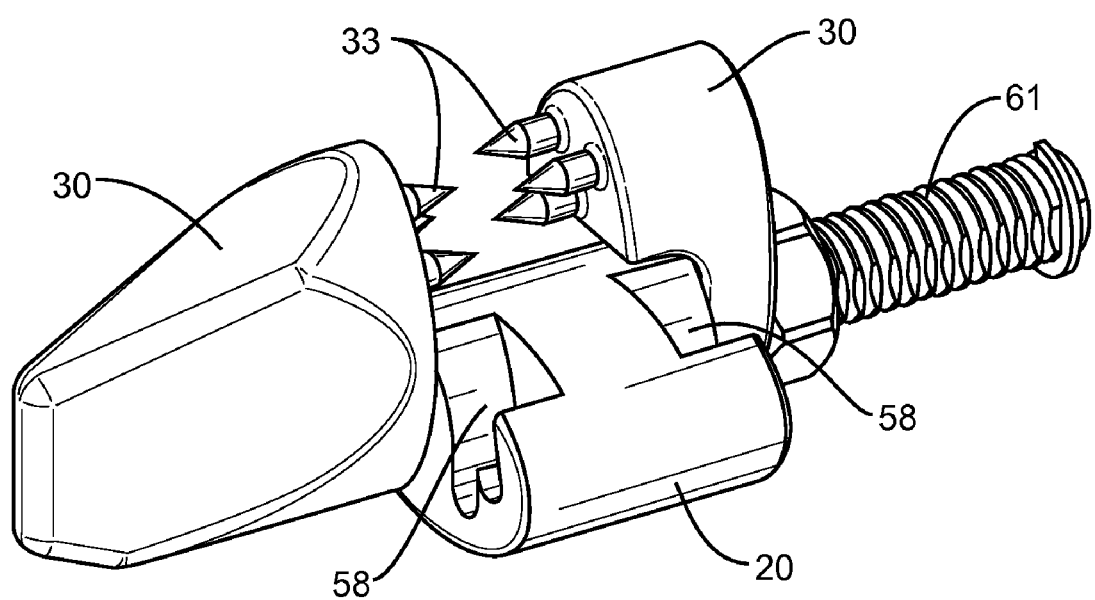
FIG. 10 is a perspective view of an implant in a deployed orientation according to one embodiment.

FIG. 10 includes the body 20 with a pair of recesses 58 sized to receive the teeth 33. The recesses 58 extend into the body 20 from an outer edge. In a closed orientation, the body 20 is aligned with the wings 30 (similar to the configuration of FIG. 8) with the teeth 33 positioned in the recesses 58. Deployment includes the relative movement between the body 20 and wings 30 about the rod 61 such that the wings 30 extend outward with the teeth 33 exposed to engage with the superior spinous process.

Figure 11:
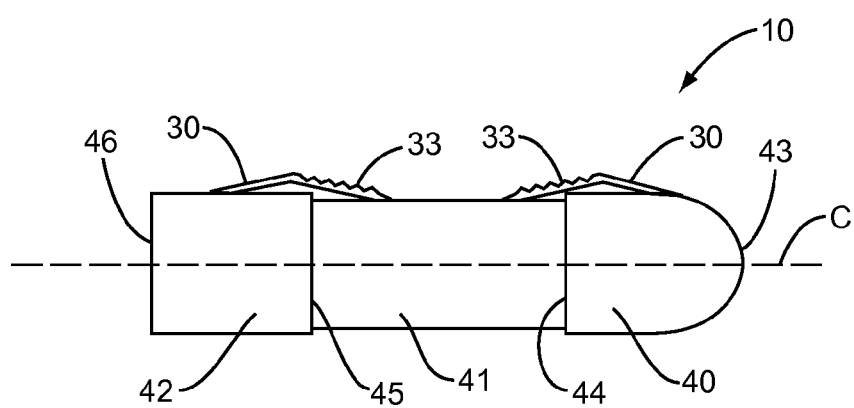
FIG. 11 is a side view of an implant in a closed orientation according to one embodiment.
Figure 12:
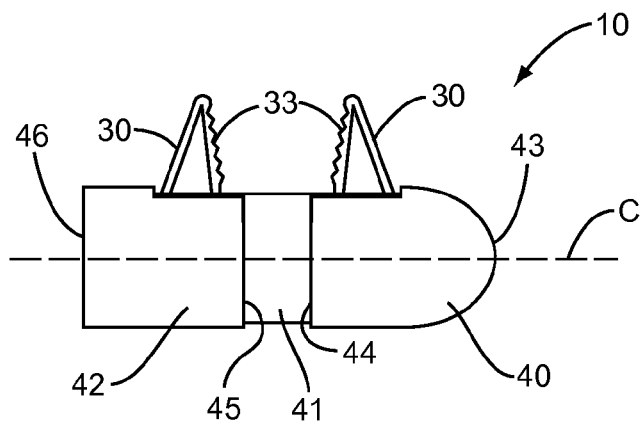
FIG. 12 is a side view of an implant in a deployed orientation according to one embodiment.
Figure 13:
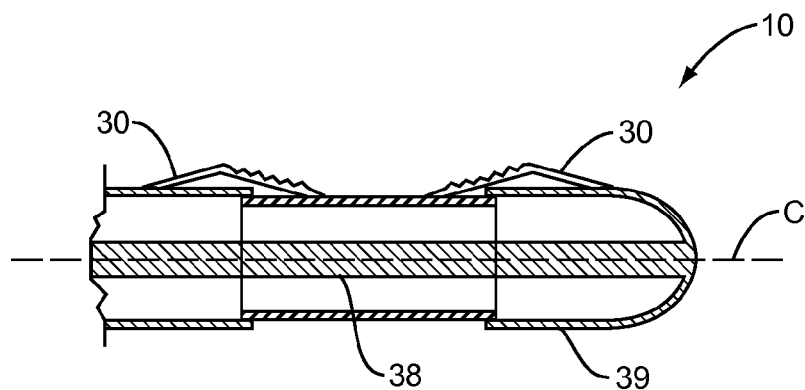
FIG. 13 is a cross section of an implant in a closed orientation according to one embodiment.

FIGS. 11-13 include an implant 10 with a pair of wings 30 that deploy to an open orientation by axial compression of the implant 10. The wings 30 are each positioned on the same side of the implant 10 and are configured to engage with opposing sides of the spinous process of the first vertebral member 100 during deployment. One or both wings 30 may include teeth 33 on an inner surface to facilitate the engagement with the spinous process.

In one embodiment as illustrated in FIGS. 11 and 12, the implant 10 includes a distal section 40, intermediate section 41, and a proximal section 42 aligned along a longitudinal axis C. The distal section 40 includes a first end 43 and a second end 44, and the proximal section 42 includes a first end 45 and a second end 46. The intermediate section 41 is coupled between second end 44 and first end 45. The wings 30 are positioned along the superior surface with the distal wing 30 straddling between the distal and intermediate sections 40, 41, and the proximal wing 30 straddling between the proximal and intermediate sections 42, 43. The sections 40, 41, 42 are sized to allow relative axial movement. In one embodiment, the intermediate section 41 is sized to fit within the interior of the distal and proximal sections 40, 42.

The implant 10 is configured to be deformed under the influence of an axial load that causes relative axial movement between the distal and intermediate sections 40, 41, and between the intermediate and proximal sections 41, 42. The deformation causes the wings 30 to deploy outward away from the sections to be positioned on the lateral sides of the spinous process.

FIG. 13 includes a similar embodiment with the implant 10 including an exterior sleeve 39 that fits over an interior member 38. The exterior sleeve 39 further includes a pair of wings 30. The interior member 38 is connected to a distal section of the exterior sleeve 39. The interior member 38 may be forced in a proximal direction with the force causing the distal section of the exterior sleeve 39 to also move in the proximal direction. This movement causes the wings 30 to deploy outward away from the interior member 38 to engage with the spinous process. The exterior sleeve 39 may include one or more gaps opposite from the wings 30 to allow the distal section to move and the wings 30 to deploy.

In use, the implant 10 is positioned in the closed orientation as illustrated in FIGS. 11 and 13. The wings 30 may include a slight fold while in the closed orientation to facilitate deployment. The implant 10 is inserted into the interspinous space 120 with the distal wing 30 moved past the spinous process of the first vertebral member 100. Once positioned, an axial load is applied to the implant 10 causing the wings 30 to deploy away from the longitudinal axis C of the implant 10 as illustrated in FIG. 12. The axial load deploys the wings 30 and moves the wings 30 along the lateral sides of the spinous process 100. In the embodiment of FIGS. 11 and 12, the movement of the wings 30 towards each other is caused by the compression of the intermediate section 41. The movement of the wings 30 in the embodiment of FIG. 13 is caused by the compression of the exterior sleeve 39.

One type of implant that deforms is the Aperius implant available from Medtronic Spinal and Biologics of Sunnyvale, Calif. Examples of an implant that deforms under the influence of an axial load are disclosed in U.S. Patent Application Serial No. 2008/0147192 herein incorporated by reference.

Figure 14:
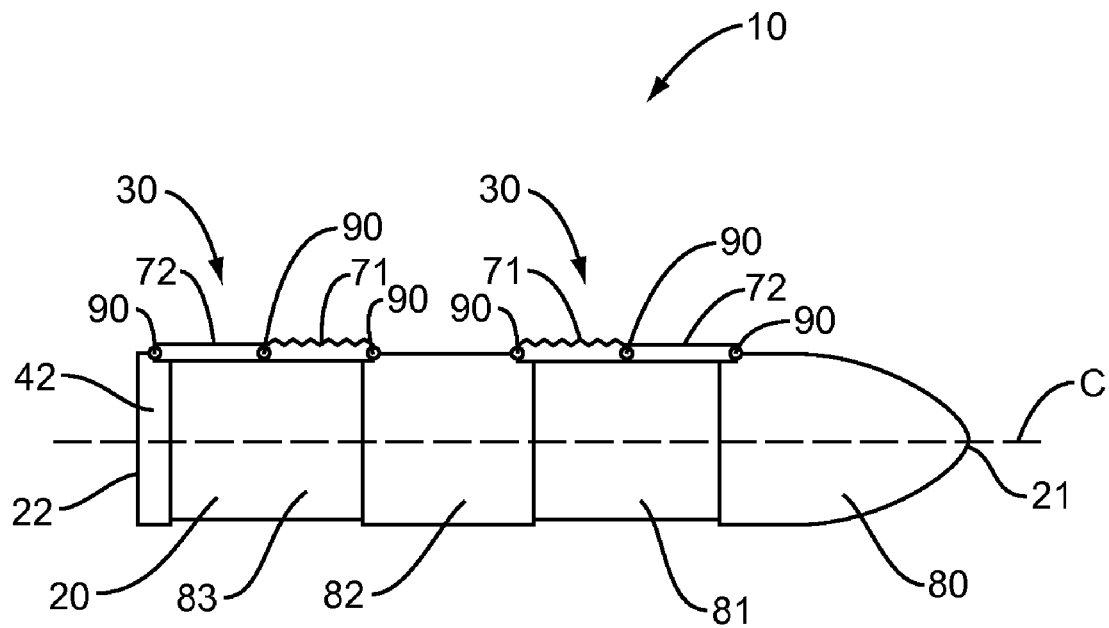
FIG. 14 is a side view of an implant in a closed orientation according to one embodiment.
Figure 15:
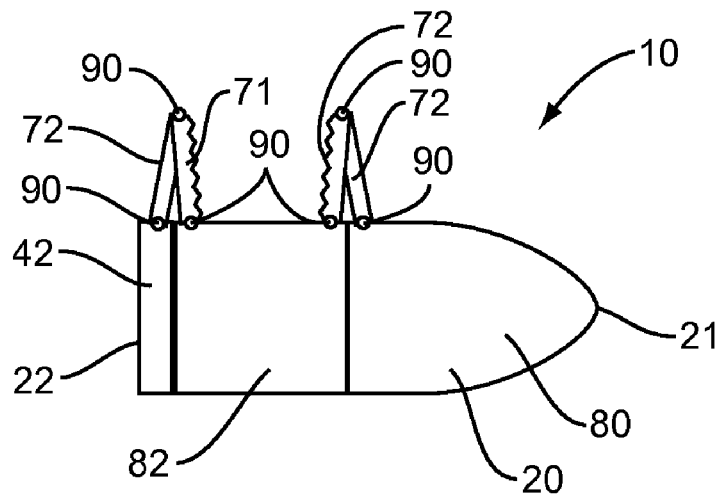
FIG. 15 is a side view of an implant in an open orientation according to one embodiment.

FIGS. 14 and 15 include an implant 10 that deploys upon application of an axial load. Implant 10 includes a proximal section 42 and telescoping sections 80-83 positioned along the longitudinal axis C and form the body 20. In this embodiment, section 81 fits within one or both of sections 80 and 82, and section 83 fits within section 82. The first section 80 includes a tapered shape with a pointed first end 21 to facilitate insertion into the patient.

Wings 30 are positioned on the superior side of the body 20 and each include a pair of links 71, 72 connected together at a pivot 90. The links 71, 72 are further pivotally connected to the body 20 with at additional pivots 90. The links 71 may further include teeth 33 to engage with the spinous process of the first vertebral member 100.

The implant 10 is inserted into the patient in the closed orientation as illustrated in FIG. 14. The shape of the body 20 and the tapered first section 80 facilitates the insertion. The implant is inserted an amount with the section 82 approximately aligned in the space 120. In the closed orientation, the links 71, 72 are aligned in a straight line.

Once positioned, an axial load is applied to the implant causing the sections 80-83 to telescope together. As illustrated in FIG. 15, section 81 moves into one or both of sections 80 and 82, and section 83 moves into section 82. The sections 80, 82 may move completely into the other sections as illustrated in FIG. 15, or move partly into the other sections.

The wings 30 are attached to different sections to cause deployment. The first wing 30 includes the first link 71 connected to section 82 and the second link 72 connected to section 80. The second wing 30 includes the first link 71 connected to section 82 and the second link 72 connected to the proximal section 41. The wings 30 deploy outward away from the main body 20 as the sections 80-83 telescope together. The height the wings 30 extend outward from the superior side of the body 20 depends upon the length of the links 71, 72, and the amount of telescoping of the different sections. In the deployed orientation, the links 71, 72 form an acute angle.

Figure 16:
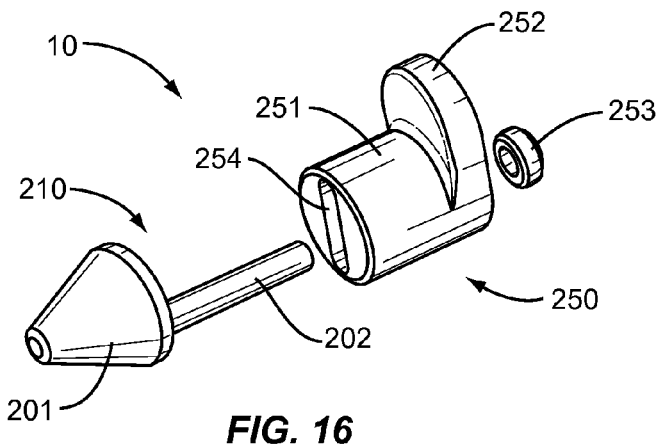
FIG. 16 is an exploded perspective view of an implant according to one embodiment.

FIGS. 16-19 illustrate a deployable implant 10 configured to be positioned in the interspinous space 120. As illustrated in FIG. 16, implant 10 includes a first section 210 and a second section 250. The first section 210 includes a first wing 201 with an extension 202 extending outward in a proximal direction. First wing 201 may be tapered to facilitate insertion into the interspinous space, and may include a variety of cross-sectional shapes and sizes. The second section 250 includes a body 251 with a second wing 252 extending outward from one side. The shapes and sizes of the body 251 and second wing 252 may vary depending upon the use. A slot 254 extends through the second section 250 and includes an elongated shape.

Figure 17:
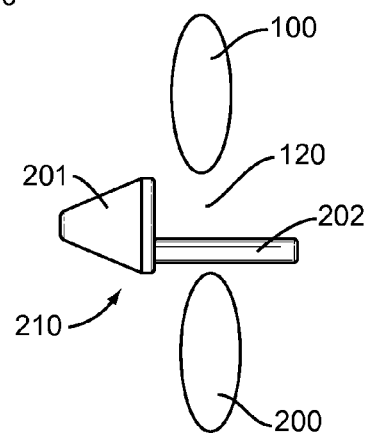
FIGS. 17-19 are side schematic views of an implant being implanted into a patient according to one embodiment.
Figure 18:
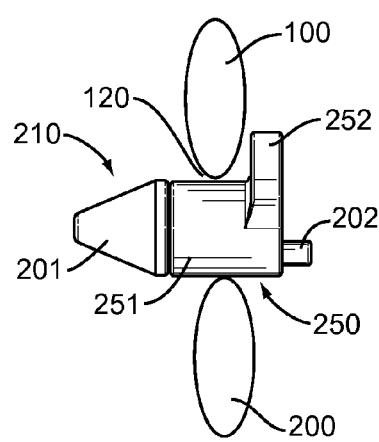

In use, the first section may be initially inserted into the patient as illustrated in FIG. 17. The wing 201 is moved through the interspinous space with the extension 202 extending within the interspinous space. As illustrated in FIG. 18, the second section 250 is inserted into the patient with the extension 202 extending through the slot 254. This positions the body 251 in the interspinous space 120 and between the spinous processes of the first and second vertebral members 100, 200, with the wings 201, 252 on opposing lateral sides of the interspinous space 120.

Another insertion method may include attaching second section 250 to the first section 210 prior to fully inserting the first section 210. The wing 201 may be positioned between the spinous processes, or even on a near side of the spinous processes when the sections 210, 250 are connected together. In yet another embodiment, the sections 210, 250 are connected together prior to insertion into the patient.

Figure 19:
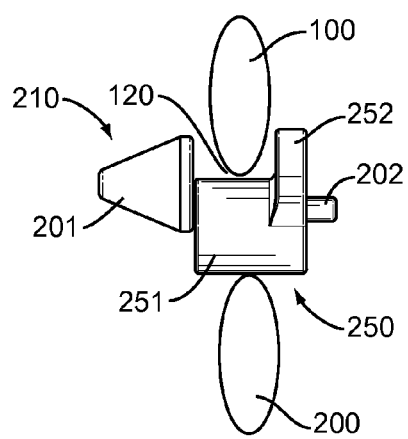

As illustrated in FIG. 19, the second section 250 may be translated in an inferior-superior plane. This may occur by relative movement of the extension 202 within the slot 254. This movement results in the wing 201 now extending upward beyond the body 251 to extend along a lateral side of the spinous process. The fastener 253 is attached to the extension 202 to secure the sections 210, 250 together. Connection of the fastener 253 may also move the sections 210, 250 together and into engagement with the spinous process. This engagement also secures the relative positions of the sections 210, 250. Teeth may be positioned on the inner surface of one or both wings 201, 252 to facilitate the contact. In the event the wings 201, 252 do not secure the relative positions of the sections 210, 250, a plug may be inserted into the slot 254 to prevent the extension 202 from translating in the inferior-superior plane.

The embodiments of FIGS. 16-19 include the wing 252 extending outward from one side of the body 251. The wing 252 may also extend outward from the opposing side of the body 251. Further, wing 252 may include various lengths to facilitate placement of the implant 10 in the interspinous space 120.

FIGS. 16-19 include deployment of the leading wing by moving the extension 202 along the slot 254. Another deployment structure includes the extension 202 attached to the wing 201 at a point offset from a longitudinal center line of the wing 201. The extension 202 extends through an aperture in the second section 250. The aperture may be offset from a longitudinal center line of the second section, is sized for rotation of the extension 202, and may or may not provide for sliding movement. Deployment includes rotation of the extension 202 by the surgeon which in turn causes the wing 201 to rotate. The offset positioning of the extension 202 results in the wing 201 extending outward beyond the surface of the body 251 to be positioned along a lateral side of the spinous process.

In a similar embodiment, the first section 210 includes a recess sized to receive the leading end of the body 251. Attachment of the first and second sections 210, 250 includes the leading end of the body 251 being inserted into the recess.

In the various embodiments, the body 20 may be wrapped in cushioning outer sleeve or coated with a compliant material. The body 20 may also be comprised of materials that are closer in stiffness to the first and second vertebral members 100, 200 to prevent subsidence of the implant 10. This is important in embodiments in which the body 20 contacts the sacrum, and especially for contact with the sacrum lamina which are relatively weak. These materials may have a Modulus of Elasticity (MOE) that is particularly matched with the vertebral members 100, 200. According to one particular embodiment, the difference of the MOE of the material and the vertebral members 10, 200 is not greater than about 30 GPa. In other embodiments, the difference is less, such as not greater than about 15 GPa, not greater than about 5 GPA, or not greater than about 1 GPa. Examples of compliant material include but are not limited to silicone, polyaryletheretherketone (PEEK), polyeurathane, and rubber.

Figure 20:
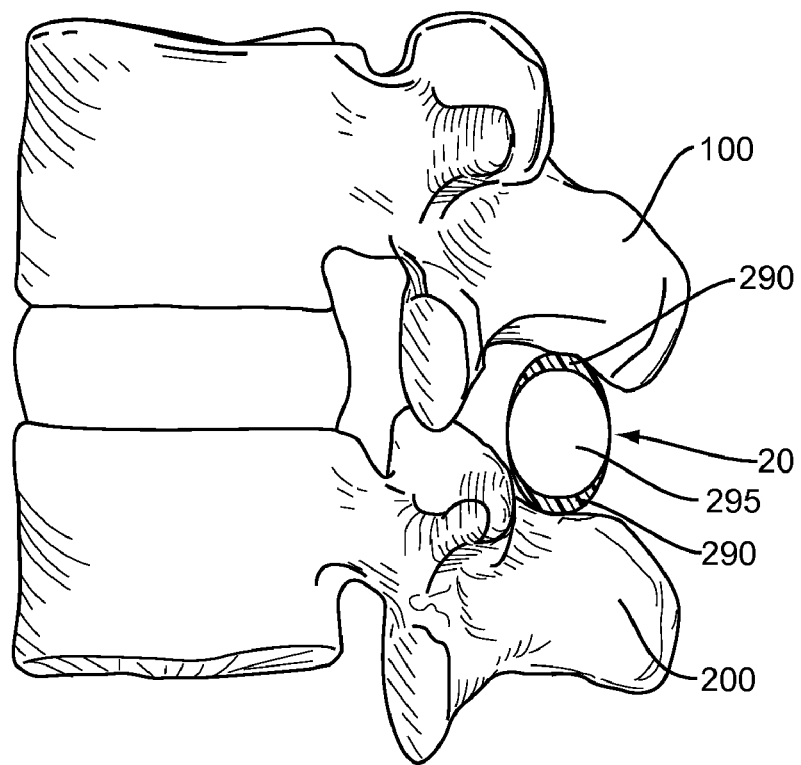
FIG. 20 is a schematic cross section of a body positioned within an interspinous space according to one embodiment.

The material may be positioned to facilitate placement of the body 20 within the interspinous space. FIG. 20 includes a schematic side view of the body 20 positioned within the interspinous space 120 with material 290 on the superior and inferior sides illustrated in cross section. The wing has been removed from the implant 10 in FIG. 20 to facilitate viewing of the body 20. The body 20 includes a core 295 with material 290 positioned on the superior and inferior sides. Positioning of the material 290 at these sides facilitates placement of the implant 10 as anterior as possible. The core 295 may be solid or hollow. The material 290 may be placed on one or both of the inferior and superior sides.

The implants 10 may be implanted within a living patient for the treatment of various spinal disorders. The implant 10 may also be implanted in a non-living situation, such as within a cadaver, model, and the like. The non-living situation may be for one or more of testing, training, and demonstration purposes.

In various embodiments, the implant 10 may be positioned in the patient with the wings 30 extending superiorly outward to contact against the spinous process of the superior vertebral member 100. The implant 10 may also be positioned in an opposite orientation (i.e., rotated 180 degrees) with the wings 30 extending inferiorly outward and contacting against a spinous process of the inferior vertebral member 200.

In the various embodiments, teeth may be positioned on the wings to engage with spinous processes. The teeth may include various shapes, sizes, and placements. In some embodiments, one or both of the wings do not include teeth.

In some embodiment, the wings 30 contact against a spinous process of a first vertebral member 100, and the body 20 contacts against the second vertebral member. The implant 10 may also be positioned in the patient with the body 20 spaced away from the second vertebral member such that there is no contact.

The implant 10 is inserted into the space 120 and contacts against one or more of the first and second vertebral members 100, 200. This contact may include direct contact with these members, and also indirect contact with the implant 10 directly contacting the surrounding ligaments and tissue. In both instances, the implant 10 includes a similar effectiveness for treating the spinal disorder for which it was implanted.

The implants 10 may be used in the interspinous space 120 formed between the L5 vertebra and sacrum. The implants 10 may also be positioned at other locations along the spine for spacing apart the vertebral members. Applications may also place the implant at other regions of the spine, including the cervical, thoracic, and lumbar regions.

The term "distal" is generally defined as in the direction of the patient, or away from a user of a device. Conversely, "proximal" generally means away from the patient, or toward the user. Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An implant for insertion into a patient between an L5 spinous process and a sacrum, the implant comprising:
   a body including a tapered first end and a second end, the body further including a superior side that faces towards the L5 spinous process and an inferior side that faces towards the sacrum when the implant is inserted into the patient;
   first and second recesses each extending into the body from the superior side, the recesses being spaced apart along the body with a contact surface formed between the recesses;
   a slot extending within an interior of the body between the recesses;
   a first wing positioned within the first recess and a second wing positioned within the second recess, the second wing further including an aperture;

an elongated rod positioned within the slot and through the aperture in the second wing, the rod including a first end attached to the first wing and a second end positioned outward from the second wing away from the first wing;

a fastener attached to the rod between the second end and the second wing, the fastener configured to move along the rod and force the wings to move together in a first lateral direction to reduce the distance between the wings with the first wing contacting against a first lateral side of the spinous process and the second wing contacting against a second lateral side of the spinous process;

the wings, rod, and fastener being movable in a second superior direction relative to the body between a closed orientation with a majority of the first and second wings positioned in the first and second recesses respectively and an deployed orientation with the majority of the first and second wings extending outward beyond the superior side of the body.

2. The implant of claim 1, wherein the inferior side of the body includes a compliant material that contacts against the sacrum when the implant is positioned in the patient.

3. The implant of claim 1, wherein the rod is connected to the first wing away from a midpoint of the height of the first wing.

4. The implant of claim 1, wherein the first wing is positioned vertically below the superior side of the body in the closed orientation.

5. The implant of claim 1, wherein the first and second recesses are positioned away from the tapered section of the body.

6. The implant of claim 1, wherein the recesses are wider than the first and second wings to allow the wings to move in the lateral direction to adjust the distance between the wings.

7. The implant of claim 1, wherein the first and second recesses extend completely through the body.

8. The implant of claim 1, wherein each of the wings includes teeth on an inner surface that face towards one another such that the teeth engage with the spinous process.

9. The implant of claim 1, wherein the first wing includes a first superior end and a second inferior end, both the first and second ends being positioned within the first recess in the closed orientation and the first end extending outward from the first recess and the second end being positioned within the first recess in the deployed orientation.

* * * * *